US00PP15442P2

(12) United States Plant Patent
Brown

(10) Patent No.: US PP15,442 P2
(45) Date of Patent: Dec. 21, 2004

(54) ***ARGYRANTHEMUM* PLANT NAMED 'SUPASAT'**

(50) Latin Name: *Argyranthemum frutescens*
Varietal Denomination: Supasat

(75) Inventor: Graham Noel Brown, Pennant Hills (AU)

(73) Assignee: NuFlora International Pty. Ltd., Macquarie Fields (AU)

( * ) Notice: Subject to any disclaimer, the term of this patent is extended or adjusted under 35 U.S.C. 154(b) by 0 days.

(21) Appl. No.: 10/818,494

(22) Filed: Apr. 5, 2004

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—C. A. Whealy

(57) ABSTRACT

A new and distinct cultivar of *Argyranthemum* plant named 'Supasat', characterized by its compact, mounded, upright and outwardly spreading plant habit; freely branching habit, dense and bushy plants; freely flowering habit with numerous inflorescences per plant; daisy-type inflorescence form with light purple-colored ray florets and bright yellow-colored disc florets.

1 Drawing Sheet

Botanical classification/cultivar denomination: *Argyranthemum frutescens* cultivar Supasat.

BACKGROUND OF THE INVENTION

The present invention relates to a new and distinct cultivar of *Argyranthemum* plant, botanically known as *Argyranthemum frutescens* and hereinafter referred to by the cultivar name 'Supasat'.

The new *Argyranthemum* is a product of a planned breeding program conducted by the Inventor in Cobbitty, New South Wales, Australia. The objective of the program is to create and develop new compact *Argyranthemum* cultivars with numerous inflorescences, interesting inflorescence form, and attractive ray floret coloration.

The new *Argyranthemum* originated from a cross-pollination by the Inventor in the spring of, 2000, of the *Argyranthemum frutescens* cultivar Summer Melody, disclosed in U.S. Plant Pat. No. 11,763, as the female, or seed, parent, with the *Argyranthemum frutescens* cultivar Sam, not patented, as the male, or pollen, parent. The new *Argyranthemum* was discovered and selected by the Inventor as a plant within the progeny of the stated cross-pollination in a controlled environment in Cobbitty, New South Wales, Australia in September, 2001. The selection of the new *Argyranthemum* was based on its attractive inflorescence form and ray floret coloration.

Asexual reproduction of the new *Argyranthemum* by terminal cuttings taken in a controlled environment in Cobbitty, New South Wales, Australia since September, 2001, has shown that the unique features of this new *Argyranthemum* are stable and reproduced true to type in successive generations.

SUMMARY OF THE INVENTION

The new *Argyranthemum* has not been observed under all possible environmental conditions. The phenotype may vary somewhat with variations in environment such as temperature and light intensity without, however, any variance in genotype.

The following characteristics have been repeatedly observed and are determined to be basic characteristics of 'Supasat' and distinguish the new *Argyranthemum* as a new and distinct cultivar:

1. Compact, mounded, upright and outwardly spreading plant habit.
2. Freely branching habit, dense and bushy plants.
3. Freely flowering habit with numerous inflorescences per plant.
4. Daisy inflorescence form with light purple-colored ray florets and bright yellow-colored disc florets.

Plants of the new *Argyranthemum* differed from plants of the female parent, the cultivar Summer Melody, in inflorescence form and ray floret coloration as plants of the cultivar Summer Melody have double-type inflorescences and pink-colored ray florets. Plants of the new *Argyranthemum* differ from plants of the male parent, the cultivar Sam, primarily in ray floret coloration as plants of the cultivar Sam have primrose-colored ray florets.

Plants of the new *Argyranthemum* differ from plants of the cultivar Supait339, discovered in U.S. Plant patent application Ser. No. 10/818,515, the cultivar Supalav, disclosed in U.S. Plant patent application Ser. No. 10/818,517, and the cultivar Supamon, disclosed in U.S. Plant patent application Ser. No. 10/818,516, in inflorescence form and floret coloration.

Plants of the new *Argyranthemum* can be compared to plants of the cultivar Cobsing, disclosed in U.S. Plant Pat. No. 13,541. In side-by-side comparisons conducted in Cobbitty, New South Wales, Australia, plants of the new *Argyranthemum* differed from plants of the cultivar Cobsing in the following characteristics:

1. Plants of the new *Argyranthemum* were not as compact than plants of the cultivar Cobsing.
2. Ray florets of plants of the new *Argyranthemum* were darker in color than ray florets of plants of the cultivar Cobsing.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Argyranthemum.*

The photograph at the top of the sheet comprises a side perspective view of a typical flowering plant of 'Supasat' grown in a one-gallon container.

The photograph at the bottom of the sheet comprises a close-up view of inflorescences of 'Supasat'.

DETAILED BOTANICAL DESCRIPTION

The aforementioned photographs, following observations and averaged measurements describe plants grown in Encinitas, Calif., in an outdoor nursery under full sunlight during winter and spring with day temperatures about 15° C. and night temperatures about 10° C. Plants were grown for about 16 weeks when the photographs and description were taken. Plants were pinched one time about five weeks after planting. Color references are made to The Royal Horticultural Society Colour Chart, 1995 Edition, except where general terms of ordinary dictionary significance are used.

Botanical classification: *Argyranthemum frutescens* cultivar Supasat.

Parentage:

*Female or seed parent.*—*Argyranthemum frutescens* cultivar Summer Melody, disclosed in U.S. Plant Pat. No. 11,763.

*Male or pollen parent.*—*Argyranthemum frutescens* cultivar Sam, not patented.

Propagation:

*Type.*—Terminal vegetative cuttings.

*Time to initiate roots.*—About 10 days at 20° C.

*Time to produce a rooted cutting.*—About three weeks at 20° C.

*Root description.*—Fibrous, fine; white in color.

*Rooting description.*—Freely branching, dense.

Plant description:

*General appearance.*—Inverted triangle; compact, mounded, upright and outwardly spreading plant form with dense foliage and inflorescences held above and beyond the foliage. Vigorous growth habit.

*Plant height.*—About 28 cm.

*Plant width.*—About 50 cm.

*Lateral branch description.*—Quantity per plant: About 14 primary lateral branches; each with about seven or eight secondary lateral branches. Length: About 25.5 cm. Diameter: About 6 mm. Internode length: Vegetative stems, about 1 cm; flowering stems, about 1.8 cm. Aspect: Upright and outwardly spreading. Texture: Smooth, glabrous. Color: 146B.

*Foliage description.*—Arrangement: Alternate, simple. Length: About 6.5 cm. Width: About 3.6 cm. Shape: Pinnatifid, deeply and finely incised. Apex: Acute. Base: Attenuate. Margin: Entire; deeply and finely incised; sinuses parallel. Texture, upper and lower surfaces: Smooth, glabrous. Venation pattern: Pinnate. Petiole length: About 1.5 cm. Petiole diameter: About 2.5 mm. Petiole texture, upper and lower surfaces: Smooth, glabrous. Color: Developing and fully expanded foliage, upper surface: 147A. Developing and fully expanded foliage, lower surface: 147B. Venation, upper and lower surfaces: 147B. Petiole, upper and lower surfaces: 147B.

Inflorescence description:

*Appearance.*—Daisy-type inflorescence form with ligulate ray florets. Disc and ray florets develop acropetally on a capitulum. Inflorescences held upright and outwardly on terminal and axillary peduncles. Inflorescences positioned perpendicular to the peduncles. Inflorescences persistent. Inflorescences not fragrant.

*Flowering response.*—Under natural conditions, plant flower from spring to early fall in Southern California; plants flower continuous during this period.

*Inflorescence longevity.*—Inflorescences last about ten days on the plant.

*Quantity of inflorescences.*—Freely flowering, about eleven buds and open inflorescences per lateral branch.

*Inflorescence size.*—Diameter: About 4.3 cm. Depth (height): About 1.5 cm. Diameter of disc: About 1.3 cm. Receptacle height: About 7 mm. Receptacle diameter: About 1.4 cm.

*Inflorescence buds, at stage of showing color.*—Height: About 1 cm. Diameter: About 9 mm. Shape: Roughly ovoid. Color: 155A.

*Ray florets.*—Quantity per inflorescence: About 24 arranged in a single whorl. Shape: Ligulate. Length: About 2 cm. Width: About 4 mm. Apex: Emarginate. Base: Acute. Margin: Entire. Texture, upper and lower surfaces: Smooth, satiny. Aspect: Initially upright; when mature, about 50 to 55° from vertical. Color: When opening, upper surface: Close to 78B. When opening, lower surface: Close to 75D. Fully opened, upper surface: Close to 78C; color becoming closer to 77B to 77C. Fully opened, lower surface: Close to 75D.

*Disc florets.*—Arrangement: Massed at the center of the inflorescence. Quantity per inflorescence: About 150. Shape: Tubular; apex, five-pointed; base, fused. Length: About 7 mm. Diameter, apex: About 1.5 mm. Diameter, base: Less than 1 mm. Color: Apex: 7A to 7B. Mid-section: 145C. Base: 145D.

*Involucral bracts* (*phyllaries*).—Appearance: Scale-like; margins, papery. Quantity per inflorescence: About 20. Length: About 2 mm. Width: About 1.5 mm. Shape: Elliptic. Apex: Acute. Base: Truncate. Margin: Entire. Texture, upper and lower surfaces: Glabrous, smooth. Color, upper surface: 144C. Color, lower surface: 144B.

*Peduncle.*—Strength: Moderately strong; wiry. Aspect: Upright to about 45° from vertical. Length, terminal inflorescence: About 6.2 cm. Diameter: About 1 mm. Texture: Smooth, glabrous. Color: 144A.

*Reproductive organs.*—Androecium: Present on disc florets only. Quantity per floret: Five. Anther shape: Oblong. Anther length: Less than 1 mm. Anther color: 14A. Amount of pollen: Scarce. Pollen color: 14A. Gynoecium: Present on ray and disc florets. Quantity per floret: One. Pistil length: About 7 mm. Stigma shape: Two-parted. Stigma color: 12A. Style length: About 3 mm. Style color: 145D. Ovary color: 145D. Seed/fruit: Seed and fruit production has not been observed.

Disease/pest resistance: Resistance to pathogens and pests common to *Argyranthemums* has not been observed on plants grown under commercial conditions.

Temperature/weather tolerance: Plants of the new *Argyranthemum* have been observed to be tolerant to rain, wind and to temperatures from −1 to 30° C.

It is claimed:

1. A new and distinct cultivar of *Argyranthemum* plant named 'Supasat', as illustrated and described.

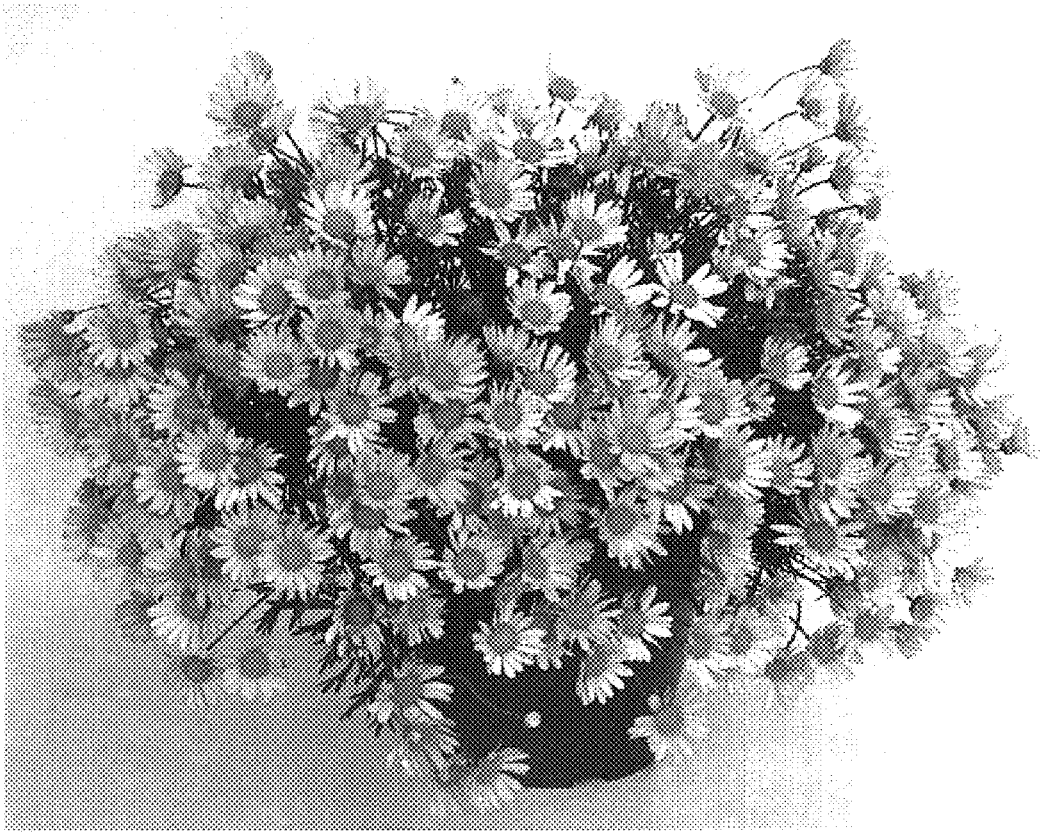
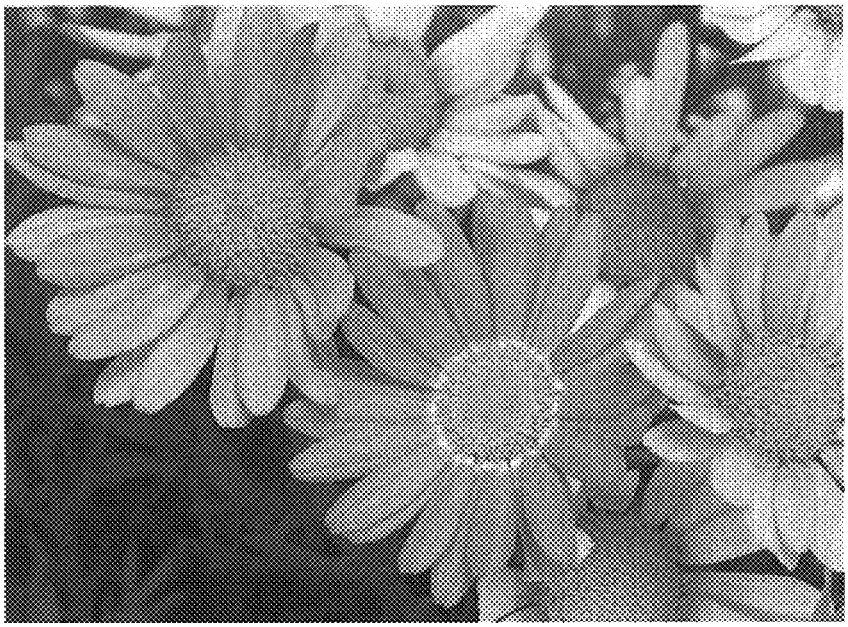

* * * * *